United States Patent [19]

Berssen et al.

[11] Patent Number: 5,386,287

[45] Date of Patent: Jan. 31, 1995

[54] DEVICE FOR AUTOMATICALLY EVALUATING A PLURALITY OF PROBE INGREDIENTS BY MEANS OF CHEMICAL SENSORS

[75] Inventors: Johannes Berssen; Clemens Hanschke, both of Berlin; Michael Kaczor, Kaarst; Hermann-Josef Klein, Schwalmtal; Michael Maczkowiak; Wolfgang Schmitt, both of Berlin, all of Germany

[73] Assignee: Dr. Bruno Lange GmbH, Germany

[21] Appl. No.: 193,623

[22] Filed: Feb. 8, 1994

Related U.S. Application Data

[63] Continuation of Ser. No. 853,786, Mar. 19, 1992, abandoned.

[30] Foreign Application Priority Data

Mar. 20, 1991 [DE] Germany ............... 4109118

[51] Int. Cl.6 ................. G01J 3/42; G01N 21/03
[52] U.S. Cl. ..................... 356/326; 356/414; 356/246; 356/427
[58] Field of Search ............ 356/319, 323, 325, 326, 356/328, 407, 414, 418, 246, 416, 427

[56] References Cited

U.S. PATENT DOCUMENTS

| | | | |
|---|---|---|---|
| 3,704,953 | 12/1972 | Carter et al. | 356/326 |
| 3,770,382 | 11/1973 | Carter et al. | 356/246 |
| 3,971,630 | 7/1976 | Sandrock et al. | 356/409 |
| 4,066,362 | 1/1978 | Carter | 356/409 |
| 4,135,883 | 1/1979 | McNeil et al. | 494/10 |
| 4,249,826 | 2/1981 | Studievic et al. | 356/246 |
| 4,795,613 | 1/1989 | Azuma et al. | 356/246 |
| 5,098,661 | 3/1992 | Froehlich et al. | 356/246 |

*Primary Examiner*—F. L. Evans
*Attorney, Agent, or Firm*—Pearne, Gordon, McCoy & Granger

[57] ABSTRACT

Device for the automatic evaluation of a plurality of test sample components, in particular within the field of water and sewage water analysis, comprising at least one chemical sensor into which the test sample component(s) is/are placed, and comprising a measuring device to determine the measurable variables which are characteristic for the test sample component(s), characterized in that each sensor is provided with a coding region for information regarding the measurable variable to be determined, and in that a reading device, for the evaluation of the coding region, and a monitoring device, which is connected to the reading device and the measuring device, are provided, wherein the monitoring device adapts the measuring device to the measurable variable to be determined on the basis of the reading supplied by the reading device.

13 Claims, 1 Drawing Sheet

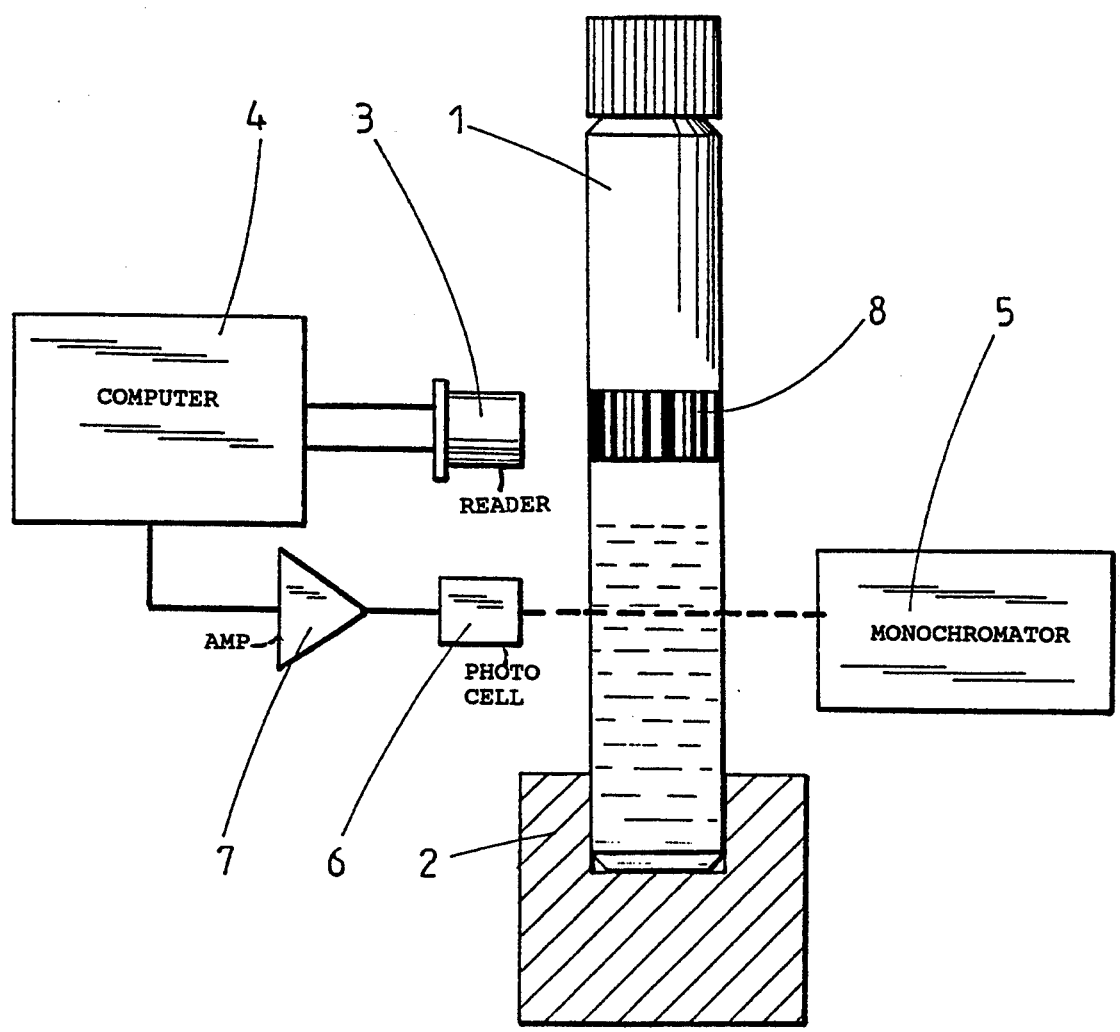

DEVICE FOR AUTOMATICALLY EVALUATING A PLURALITY OF PROBE INGREDIENTS BY MEANS OF CHEMICAL SENSORS

This is a continuation of application Ser. No. 07/853,786, filed Mar. 19, 1992 now abandoned.

The invention relates to a device for the automatic evaluation of a plurality of components of test samples, comprising at least one chemical sensor into which the test sample component(s) is/are placed, and comprising a measuring device to determine the measurable variables which are characteristic for the test sample component(s).

Such devices are used widely in industry, but they gain particular significance with regard to environmental technology, and there, principally, for water and sewage water analysis. In order to ensure the purity of waters, it is important that municipal sewage purification plants and industrial concerns can control the composition of their waste water. In this regard, it must be possible to carry out control on site, in order that the respective sewage purification plant can, immediately the measuring results are to hand, be controlled such that the limit values specified by the legislator are observed. For routine tasks of this kind, the total range of measuring instruments must be easy to operate; mix-ups may also not arise during the evaluation.

It is therefore the object of the invention to provide a device for the automatic analyzing of a plurality of specimen substances, which device is user-friendly and continues to supply accurate evaluation results.

This object is met by a device of the kind mentioned at the outset and having the features and advantageous developments set out in the claims.

According to the invention, each sensor is provided with a coding region for information concerning the measurable variable to be determined, in addition, a reading device, for the evaluation of the coding region, and a monitoring device, which is connected to the reading device and the measuring device, are provided, wherein the monitoring device adapts the measuring device to the measurable variable to be determined, on the basis of the reading supplied by the reading device. In the case of an appropriately selected measuring device, an apparatus of this kind is available for the quantitative measuring of the components of water. In this regard, the combination of sensor and automatic evaluation is particularly suitable, since a plurality of measurable variables or parameters can be determined in parallel. Using a device according to the invention, it is possible, at present, to measure about forty parameters. Even with the plurality of values which can be analyzed, there can be no confusion between the sensors, due to the coding regions which are provided. A source of errors can, therefore, not be expected from this quarter.

The measuring device is, preferably, a photometer since, thereby, the sensor can be evaluated for the selective analysis of test sample components.

In addition, the sensor is, advantageously, a cuvette, preferably of glass, into which the prepared selective indicator reagents are filled, such that the chemical sensors thus prepared can be used directly for the analysis. In this regard, the reagents are present in fluid and partially in lyophilized form.

The coding region may be a label or a magnetic strip on which the information is printed. In this regard, the information expediently comprises substance parameters, substance-specific data for the evaluation, wavelength ranges for the light to be passed through, and the like.

The reading procedure can be undertaken particularly reliably and simple when the coding region is a bar code strip or a magnetic strip.

For the specific field of application in water and sewage water analysis, it is advantageous when the coding region is resistant to chemicals and/or is unaffected by changes in temperature, in particular that it is resistant to chromic-sulphuric acid and temperature-stable up to 160° C. This, because chromic-sulphuric acid is used as a fluid reagent in CSB determining. Said reagent, mixed with the water specimen, is boiled for a period of two hours at 148° C. The coding region of the sensor should measure up to such extreme stress.

Advantageously, the photometer is designed to have an automatic wavelength adjustment. After identifying the measurable variable to be determined from the coding region, the monitoring device can then automatically adjust the wavelength range required for the evaluation and, after the measuring procedure, the photometer indicates the concentration of the measurable variable of interest.

Advantageously, the automatic wavelength adjustment is carried out by a monochromator or optic filter which is controlled by the monitoring device. The automatic wavelength adjustment is then carried out using a stepping motor which actuates the monochromator or the optic filter, in conjunction with, for example, a microprocessor. An adjustable luminescent diode, which functions as a receiver, is used to adjust the zero position of the monochromator.

Particularly advantageously, each sensor is rotatable through a preselected angular range. When the sensor is designed as a cuvette, i.e. like a test tube, this rotation expediently takes place about the longitudinal axis. This permits a completely accurate scanning operation during the reading of the coding region, in particular when the latter is designed as a bar code strip or magnetic strip; in addition, when the cuvette is rotated during the measuring and evaluating, the measuring can be carried out at different points of the glass body of the sensor. The measuring result is considerably improved by a computational averaging procedure or a different suitable error-processing procedure, since inaccuracies, which arise owing to differences in the optical quality of the glass body at different points, are compensated for.

According to the invention, said device for the automatic evaluation of a plurality of test sample components is used in that a sensor, which is filled with the specimen of interest, which sensor is, for example, a glass cuvette with a selective reagent and is provided, on its outside, with a bar code strip or magnetic strip comprising the information which is required for the evaluation of the components to be examined, is initially rotated through an angular section, the arc length of which corresponds to the length of the bar code strip, for example 360°, whereby, during this rotation, the information provided in the coding region is read, processed and used for the control of the measuring device, for example to adjust a specific wavelength or a specific wavelength range, whereupon the measuring is carried out during a further rotation of the cuvette through a, likewise, predetermined angular section.

The invention is to be described in more detail hereinafter, merely by way of example, with reference to the attached drawing. In this regard, the single Figure diagrammatically shows the design of a device according to the present invention.

A chemical sensor 1, which is equipped to be a cuvette and contains the indicator reagent and is filled with specimen substance, is supported in its bottom region in a rotating device 2. Approximately in the region of the centre line of the sensor 1, a bar code strip 8 is provided and is arranged substantially in a plane perpendicular to the longitudinal axis of the sensor 1, such that the strip of the bar code extend parallel to the longitudinal axis of the sensor 1. A reading device 3 for the bar code is arranged at a distance from the sensor 1 opposite the bar code strip 8. Said reading device 3 is connected to a equipment computer 4 which takes over the evaluation of the information read, for the control of the actual measuring device, being a photometer which comprises a monochromator 5, a photoelectric cell 6 and an amplifier 7. The monochromator 5 and the photoelectric cell 6 are arranged opposite one another on different sides of the sensor 1, such that the light emitted by the monochromator 5 passes through the sensor 1 and, thus, through the specimen/reagent mixture contained therein, before it is taken up by the photoelectric cell 6. The signals from the photoelectric cell 6 are intensified by the amplifier 7 and are then routed to the equipment computer 4 for evaluating. The reading device 3 and the measuring device 5, 6, 7 are arranged at different levels of the sensor 1. In the case illustrated in the Figure, the monochromator 5, with the opposing photoelectric cell 6, are disposed approximately centrally between the bar code strip 8 and the bottom region of the sensor 1 supported in the rotating device 2.

Other arrangements of reading device 3 and measuring device 5, 6, 7 are also conceivable, but it will be expedient to maintain them spaced from one another in the vertical direction, in order that the measuring procedure which does, of course, require the passage of light through the specimen/reagent mixture in the sensor 1, is not obstructed by the bar code strip 8 which is in alignment with the reading device 3.

When the sensor 1 is then rotated, the reading device 3 initially gathers the information located on the bar code strip 8 and directs it to the equipment computer 4. On the basis of the information, said computer identifies only the measurable variables of interest and adjusts the measuring device 5, 6, 7 in accordance therewith. While the sensor 1 continues to rotate, the analysis is carried out in that light emitted from the monochromator 5 is directed through the sensor 1 on to the photoelectric cell 6. The quantitative proportion of impurities can be deduced from the extinction behaviour of the sensor (specimen/reagent mixture) at the determined wavelength or in the observed wavelength range.

Immediately thereafter, without undertaking any modifications of the measuring device, a further sensor can be placed in position in the rotating device 2, whereupon the process can be carried out anew.

We claim:

1. Device for the automatic evaluation of a plurality of test sample components, comprising at least one sensor (1) in which the test sample component(s) is/are placed, and a measuring device to determine the measurable variables which are characteristic for the test sample components, characterized in that said sensor (1) has an axis and a rotating device (2) is provided to rotate the sensor about said axis through a predetermined angular range during a determination by said measuring device; each sensor (1) is provided with a coding region (8) for information concerning the measurable variable to be determined; and a reading device, for the evaluation of the coding region (8), and a monitoring device (4), which is connected to the reading device (3) and the measuring device (5, 6, 7) are provided, wherein the monitoring device (4), on the basis of the reading supplied by the reading device (3), adapts the measuring device (5, 6, 7) to the measurable variable to be determined.

2. Device according to claim 1, characterized in that the measuring device (5, 6, 7) is a photometer.

3. Device according to claim 2, characterized in that the sensor (1) is a test tube and contains a selective reagent for a specific parameter.

4. Device according to claim 3, characterized in that the coding region (8) is a label on which the information is printed.

5. Device according to claim 4, characterized in that the coding region (8) is a bar code strip or a magnetic strip.

6. Device according to claim 5, characterized in that the coding region (8) is resistant to chemicals and/or unaffected by changes in temperature.

7. Device according to claim 6, characterized in that the coding region (8) is resistant to chromic-sulphuric acid.

8. Device according to claim 7, characterized in that the coding region (8) is temperature-stable up to about 160° C.

9. Device according to claim 8, characterized in that the photometer (5, 6, 7) has an automatic wavelength adjustment for measuring simultaneously at a plurality of different wavelengths.

10. Device according to claim 9, characterized in that the automatic wavelength adjustment is carried out via a monochromator (5) or optical filter controlled by the monitoring device (4).

11. Device according to claim 1, characterized in that the reading device (3) comprises a photometer for the evaluation of the coding region (8).

12. Use of the device according to claim 11 for the automatic analyzing of a plurality of specimen substances, whereby the sensor (1) is rotated through a predetermined angular range initially to read the coding region (8) and then to measure the measurable variable of interest.

13. Device according to claim 1, wherein the rotating device is adapted to index the sensor to a plurality of angular positions during measuring.

* * * * *